US010667845B2

(12) United States Patent
Milbrandt et al.

(10) Patent No.: US 10,667,845 B2
(45) Date of Patent: Jun. 2, 2020

(54) VERTEBRAL TETHERING

(71) Applicant: Mayo Foundation for Medical Education and Research, Rochester, MN (US)

(72) Inventors: Todd A. Milbrandt, Rochester, MN (US); A. Noelle Larson, Rochester, MN (US); Stephen D. Cassivi, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 17 days.

(21) Appl. No.: 16/031,557

(22) Filed: Jul. 10, 2018

(65) Prior Publication Data

US 2019/0021768 A1 Jan. 24, 2019

Related U.S. Application Data

(60) Provisional application No. 62/534,393, filed on Jul. 19, 2017.

(51) Int. Cl.
*A61B 17/70* (2006.01)
*A61B 17/88* (2006.01)
*A61B 17/56* (2006.01)
*A61B 90/00* (2016.01)

(52) U.S. Cl.
CPC ...... *A61B 17/7022* (2013.01); *A61B 17/7005* (2013.01); *A61B 17/7032* (2013.01); *A61B 17/7079* (2013.01); *A61B 17/885* (2013.01); *A61B 2017/564* (2013.01); *A61B 2090/3966* (2016.02)

(58) Field of Classification Search
CPC .............. A61B 17/702; A61B 17/7022; A61B 17/7083; A61B 17/82; A61B 17/842; A61B 17/8869; A61B 17/8861; A61B 17/7079

See application file for complete search history.

(56) References Cited

U.S. PATENT DOCUMENTS

| | | | | |
|---|---|---|---|---|
| 6,689,140 | B2 * | 2/2004 | Cohen | A61B 17/8861 606/103 |
| 7,922,725 | B2 * | 4/2011 | Darst Rice | A61B 17/8869 606/86 A |
| 8,080,045 | B2 * | 12/2011 | Wotton, III | A61B 17/8866 606/324 |
| 8,323,294 | B2 * | 12/2012 | Mickiewicz | A61B 17/701 606/103 |
| 8,486,114 | B2 * | 7/2013 | Gillard | A61B 17/823 606/263 |
| 8,641,736 | B2 * | 2/2014 | Marik | A61B 17/7022 606/254 |
| 9,173,685 | B2 * | 11/2015 | Lindquist | A61B 17/7049 |
| 9,433,442 | B2 | 9/2016 | Lindemann et al. | |
| 2002/0072753 | A1 * | 6/2002 | Cohen | A61B 17/8861 606/103 |
| 2006/0217715 | A1 | 9/2006 | Serhan et al. | |

(Continued)

*Primary Examiner* — Lynnsy M Summitt
(74) *Attorney, Agent, or Firm* — Fish & Richardson P.C.

(57) ABSTRACT

Scoliosis can be treated by systems for anterior vertebral body tethering described herein. In some embodiments, installation tools of a system for anterior vertebral body tethering can be used to sequentially tension segments of a tether between adjacent vertebral screws in a controllable and user-friendly manner.

19 Claims, 3 Drawing Sheets

(56) References Cited

U.S. PATENT DOCUMENTS

| | | | |
|---|---|---|---|
| 2010/0094294 A1* | 4/2010 | Gillard | A61B 17/823 606/74 |
| 2013/0072983 A1* | 3/2013 | Lindquist | A61B 17/7049 606/278 |
| 2016/0000468 A1 | 1/2016 | Samdani et al. | |
| 2016/0296265 A1 | 10/2016 | Mickiewicz et al. | |

* cited by examiner

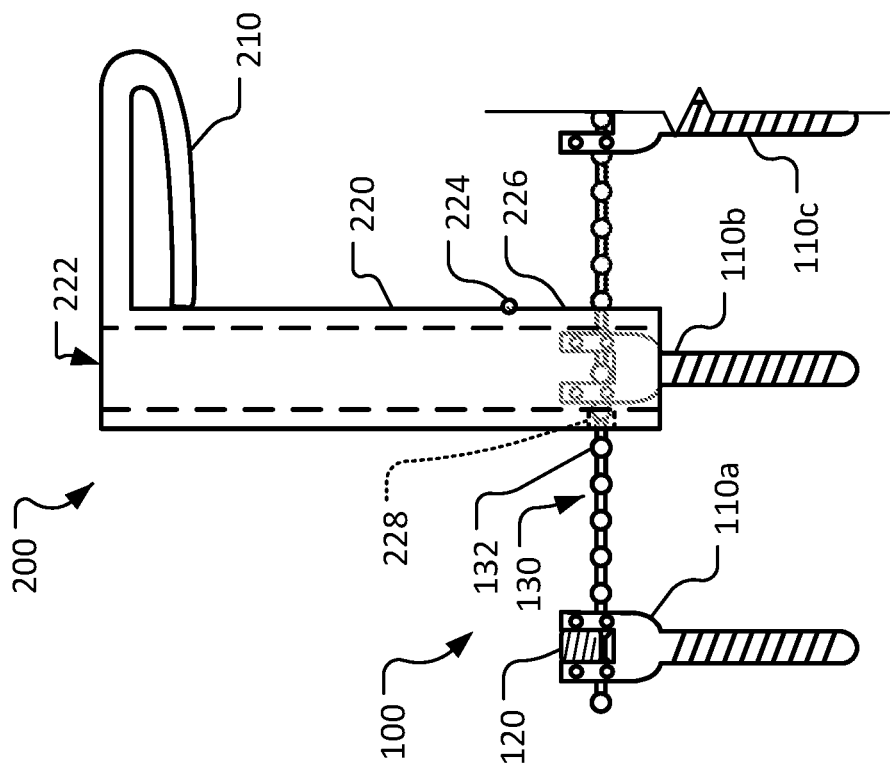
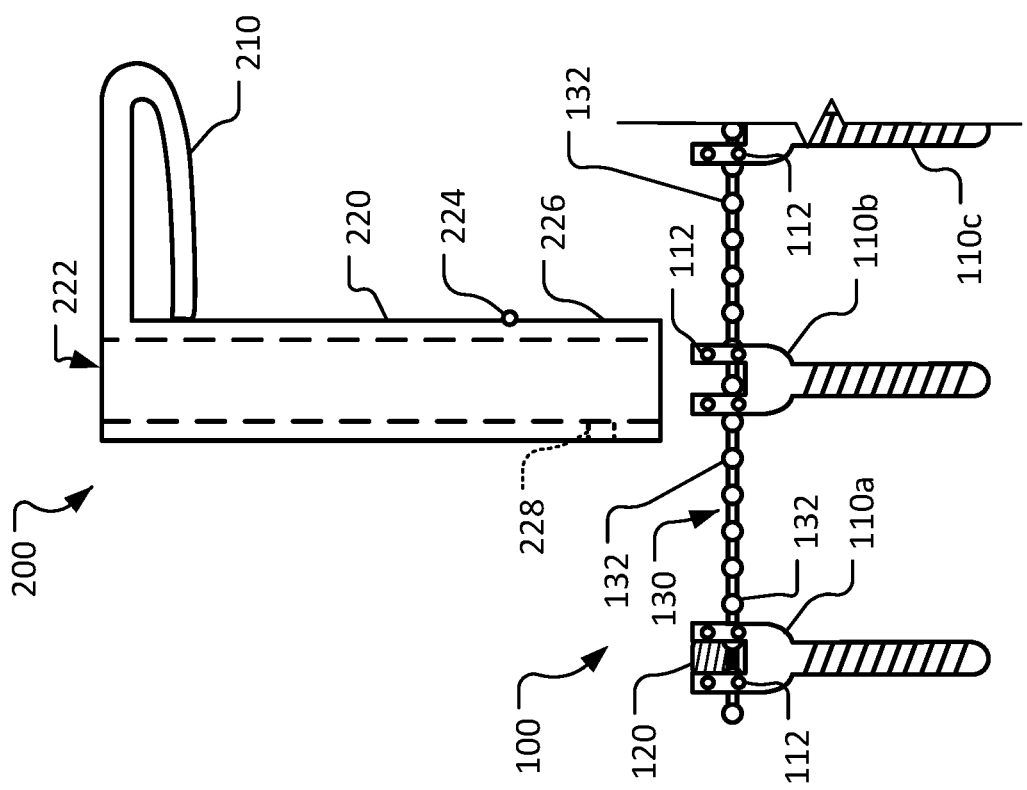
FIG. 3
FIG. 4

VERTEBRAL TETHERING

CROSS-REFERENCE TO RELATED APPLICATIONS

This application claims the benefit of U.S. Provisional Application Ser. No. 62/534,393, filed Jul. 19, 2017. The disclosure of the prior application is considered part of (and is incorporated by reference in) the disclosure of this application.

BACKGROUND

1. Technical Field

This document relates to systems for treating scoliosis and methods for their use. For example, this document relates to systems for anterior vertebral body tethering and methods for their use.

2. Background Information

Scoliosis is a sideways curvature of the spine that occurs most often during the growth spurt just before puberty. While scoliosis can be caused by conditions such as cerebral palsy and muscular dystrophy, the cause of most scoliosis is unknown.

Most cases of scoliosis are mild, but some children develop spine deformities that continue to get more severe as they grow. Severe scoliosis can be disabling. An especially severe spinal curve can reduce the amount of space within the chest, making it difficult for the lungs to function properly.

Traditionally, scoliosis is treated by a spinal fusion performed posteriorly. Spinal fusion involves techniques designed to mimic the normal healing process of broken bones. During spinal fusion, a surgeon places bone or a bonelike material within the space between two spinal vertebrae. Metal plates, screws and rods may be used to hold the vertebrae together, so they can heal into one solid unit. Because spinal fusion surgery immobilizes parts of the spine, it changes the way the spine can move. This places additional stress and strain on the vertebrae above and below the fused portion, and may increase the rate at which those areas of the spine degenerate.

SUMMARY

This document describes systems for treating scoliosis and methods for their use. For example, this document describes systems for anterior vertebral body tethering and methods for their use.

In one aspect, this disclosure is directed to a surgical tool that includes an actuator handle; a barrel extending from the actuator handle, the barrel defining a longitudinal lumen; a one-way mechanism coupled to a distal end portion of the barrel, the one-way mechanism configured to engage with a tether such that the one-way mechanism allows passage of the tether in a first direction and prevents passage of the tether in a second direction that is opposite to the first direction; and a tensioning member movably coupled to the distal end portion of the barrel, the tensioning member configured to engage with the tether and to apply tension to the tether along the first direction in response to a manual actuation of the actuator handle.

Such a surgical tool may optionally include one or more of the following features. The tensioning member may be pivotably coupled to the barrel. The actuator handle may include a ratchet mechanism. The one-way mechanism may be manually releasable from preventing passage of the tether in the second direction. The surgical tool may also include a second surgical tool having an elongate shaft that can extend into the lumen.

In another aspect, this disclosure is directed to a system for anterior vertebral body tethering. The system includes a plurality of vertebral screws, an elongate tether, and a first surgical tool. The first surgical tool includes an actuator handle; a barrel extending from the actuator handle, a distal tip portion of the barrel being releasably coupleable with each of the vertebral screws individually; and a tensioning member movably coupled to the distal end portion of the barrel. The tensioning member is configured to engage with the tether and to apply tension to the tether along a first direction in response to a manual actuation of the actuator handle.

Such a system may optionally include one or more of the following features. The system may also include a one-way mechanism coupled to a distal end portion of the barrel. The one-way mechanism may be configured to engage with the tether such that the one-way mechanism allows passage of the tether in the first direction and prevents passage of the tether in a second direction that is opposite to the first direction. The system may include a second surgical tool having an elongate shaft that can extend into a lumen defined by the barrel. The tether may include a plurality of expanded areas spaced apart from each other along the tether. The tensioning member may engage with the expanded areas of the tether. The system may also include a one-way mechanism coupled to a distal end portion of the barrel. The one-way mechanism may be configured to engage with the expanded areas of the tether such that the one-way mechanism allows passage of the tether in the first direction and prevents passage of the tether in a second direction that is opposite to the first direction.

In another aspect, this disclosure is directed to a method of treating scoliosis of a spine. The method includes: anteriorly installing vertebral screws into vertebrae of the spine such that a first vertebra of the vertebrae receives a first vertebral screw of the vertebral screws and a second vertebra of the vertebrae receives a second vertebral screw of the vertebral screws; fixedly attaching a tether to the first vertebral screw; releasably coupling a first surgical tool to the second vertebral screw and to the tether concurrently; and manually actuating the actuator handle while the distal tip portion of the barrel is releasably coupled with the second vertebral screw and the tether such that tension is applied to the tether between the first vertebral screw and the tensioning member. The first surgical tool includes: an actuator handle; a barrel extending from the actuator handle, a distal tip portion of the barrel being releasably coupleable with each of the vertebral screws individually; and a tensioning member movably coupled to the distal end portion of the barrel. The tensioning member is configured to engage with the tether and to apply tension to the tether along a first direction in response to a manual actuation of the actuator handle.

In some embodiments, the method also includes, while maintaining the tension applied to the tether between the first vertebral screw and the tensioning member, fixedly attaching the tether to the second vertebral screw such that the tension is thereafter maintained in a portion of the tether between the first vertebral screw and the second vertebral screw without needing the tensioning member to apply the tension in the portion of the tether between the first vertebral screw and the second vertebral screw.

Particular embodiments of the subject matter described in this document can be implemented to realize one or more of the following advantages. In some embodiments, spinal conditions such as scoliosis and others can be treated using the devices and methods provided herein. In some embodiments, scoliosis can be treated in a minimally invasive fashion using the devices and methods provided herein. Such minimally invasive techniques can reduce recovery times, patient discomfort, and treatment costs. Moreover, the anterior vertebral body tethering systems described herein can facilitate tensioning of the anterior tether in a precise and accurately-controllable manner, leading to improved patient outcomes. The tether tensioning mechanisms and methods are also advantageously user friendly as compared to prior tether tensioning techniques.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 3 shows an installation step of an anterior vertebral body tethering system in accordance with some embodiments provided herein.

FIG. 4 shows another installation step of the anterior vertebral body tethering system of FIG. 3.

Like reference numbers represent corresponding parts throughout.

DETAILED DESCRIPTION

This document describes systems for treating scoliosis and methods for their use. For example, this document describes systems for anterior vertebral body tethering and methods for their use.

Figure 1:
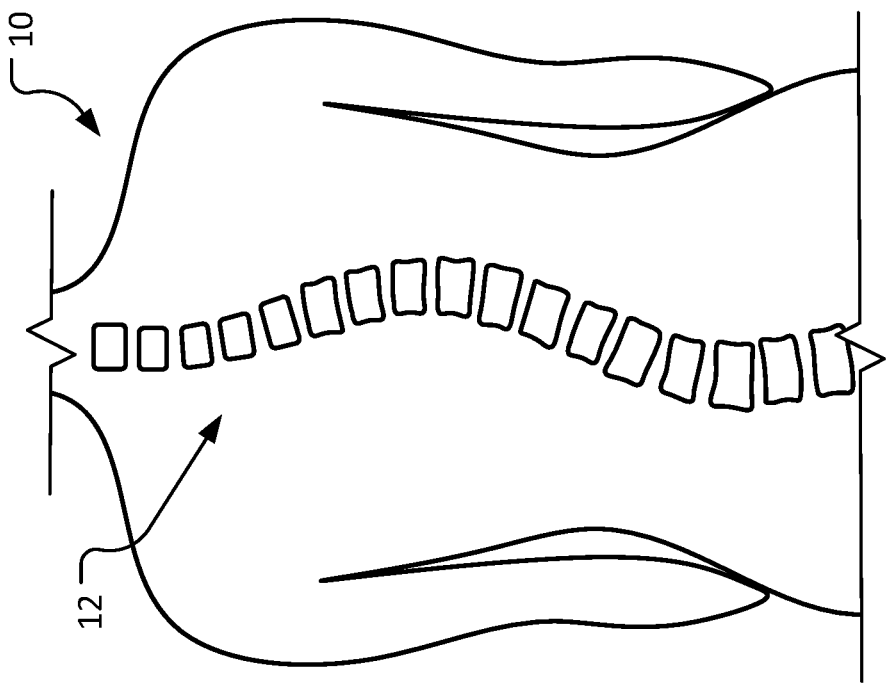
FIG. 1 is a schematic diagram of a patient with scoliosis.

Referring to FIG. 1, a patient 10 has a spine 12 that is affected by scoliosis.

Figure 2:
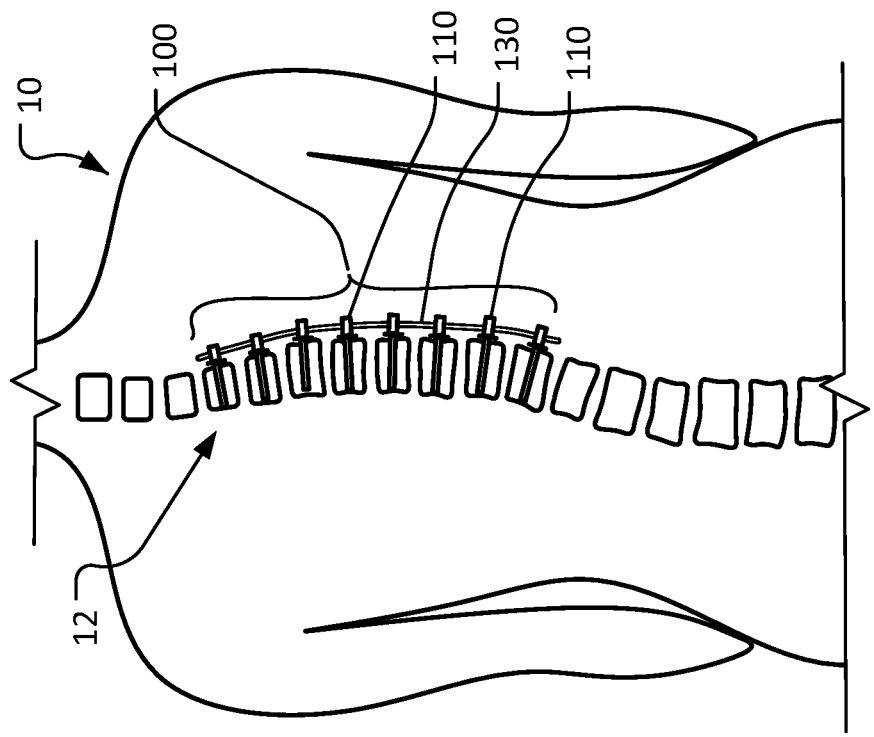
FIG. 2 is a schematic diagram of the patient of FIG. 1 after the installation of an anterior vertebral body tethering system in accordance with some embodiments provided herein.

Referring to FIG. 2, here patient 10 is being treated by an anterior vertebral body tethering system 100 in accordance with some embodiments described herein. Anterior vertebral body tethering system 100 is installed anteriorly along the outer curvature of spine 12.

An anterior vertebral body tethering surgery to implement the configuration shown in FIG. 2 involves inserting vertebral screws into the vertebrae affected by scoliosis. As described further below, the surgeon attaches a cord (tether) to each of the screws and then pulls (tensions) and secures the cord segmentally, so the vertebrae are cinched together on one side and splayed open on the other, correcting the curve. This generally aligns spine 12 and gives the vertebrae space to grow in properly. Designed to treat moderate to severe scoliosis, anterior vertebral body tethering system 100 is typically recommended for adolescents during puberty who are still growing. Anterior vertebral body tethering surgery can be performed in a minimally-invasive manner (e.g., using video-assisted thoracoscopic surgery techniques).

Figure 6:
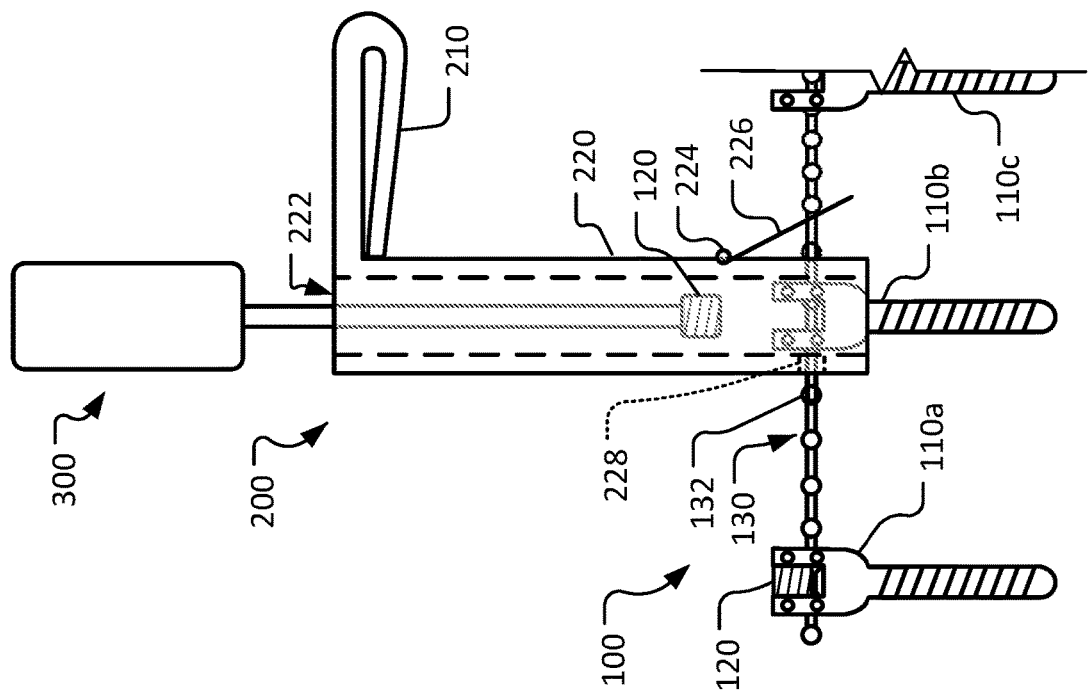
FIG. 6 shows another installation step of the anterior vertebral body tethering system of FIG. 3.

Referring also to FIG. 3, anterior vertebral body tethering system 100 includes multiple vertebral screws 110 (e.g., vertebral screw 110a, vertebral screw 110b, and vertebral screw 110c are shown in FIG. 3), multiple end caps 120, and a tether 130. In some cases, anterior vertebral body tethering system 100 also includes installation tools 200 and/or 300 (FIG. 6).

Individual vertebral screws 110 are installed into a respective vertebra (e.g., as shown in FIG. 2). The vertebrae are omitted from view in FIGS. 3-6 to provide better visualization of anterior vertebral body tethering system 100. Tether 130 extends between each vertebral screw 110. End caps 120 are used to fixedly capture tether 130 to the heads of vertebral screws 110. In the depicted configuration, a single end cap 120 is installed in vertebral screw 110a whereby tether 130 is fixedly attached to vertebral screw 110a, and tether 130 is not yet tensioned.

In some embodiments, vertebral screws 110 are non-cannulated solid screws made of stainless steel or titanium. Vertebral screws 110 may be 3-D printed using titanium with a variable porosity from a solid titanium central core that is contiguous with the head portion and the tip (which could have grooves to cut into the bone) but with gradually increasing porosity out to the edges of the screw 110 where the bone ingrowth is desired. In some embodiments, a hydroxyapatite coating may be included on vertebral screws 110 to enhance bone ingrowth. It should be understood that vertebral screws 110 are scalable to any suitable length and diameter. For example, in some cases vertebral screws 110 may have screw lengths in a range from about 20 mm to about 45 mm (without limitation). In some cases, vertebral screws 110 may have screw diameters of about 3.5 mm to about 6.0 mm (without limitation).

In some embodiments, vertebral screws 110 are blunt-tipped at the ends such that bi-cortical fixation is possible without damage to the anatomical structures on the farther side of the vertebra. The heads of vertebral screws 110 can be tulip-shaped with internal threads that can threadedly engage with externally-threaded end caps 120. The tulip shape configures the heads of vertebral screws 110 to allow lateral passage of tether 130 through the slots defined by the tulip-shaped heads. In some embodiments, the heads of vertebral screws 110 include structures such as dimples 112 that are used to facilitate releasable engagement and positional registration between vertebral screws 110 and installation tool 200.

In some embodiments, end caps 120 are threaded members resembling set screws. End caps 120 can threadedly engage with the heads of vertebral screws 110. End caps 120 can be made of metallic materials like stainless steel and titanium, or other materials including polymeric materials. In some embodiments, end caps 120 define a hex socket head that receives a socket driver such as installation tool 300 (FIG. 6). In particular embodiments, the leading end tip of end caps 120 can be concaved or otherwise specifically shaped to engage with physical features of tether 130.

The left-most vertebral screw 110a in FIG. 3 includes an end cap 120 which has been tightened relative to the head of the vertebral screw 110 to tightly capture tether 130 there between. The other two vertebral screws 110b and 110c are depicted as not having received an end cap 120 as of yet.

In some embodiments, tether 130 is an elongate flexible member with a series of bead-like expanded areas 132 that are spaced apart from each other along tether 130. In some cases, tether 130 is made of a polymeric material such as, but not limited to, polyethylene-terephthalate (PET). While expanded areas 132 of tether 130 as shown as spherical beads, in some embodiments expanded areas 132 are disks, cubes, polyhedrons, and the like. In some embodiments, tether 130 does not include any expanded areas 132.

Expanded areas 132 are scalable to any suitable size and spacing. In some examples, the size of expanded areas 132 is about 2 mm in diameter (or in a range of about 1 mm to about 5 mm) without limitation. In some examples, there is about a 2 mm spacing between expanded areas 132 (e.g., 4 mm center to center from one 2 mm diameter expanded area 132 to the next 2 mm diameter expanded area 132) without limitation. In some examples, the spacing is in a range of about 1 mm to about 6 mm, and anywhere there between, without limitation.

In some embodiments, tether 130 includes a series of radiopaque markers. For example, in some examples a discreet radiopaque marker is located at each expanded area 132. Such radiopaque markers can allow for intraoperative and/or postoperative x-ray imaging of tether 130 so that irregularities such as breaks of tether 130 can be detected non-invasively. Additionally, in some cases x-ray images of radiopaque markers at expanded areas 132 can be used for measurement of the distances between adjacent radiopaque markers at expanded areas 132 to facilitate estimation of the tension of segments of tether 130 between the adjacent radiopaque markers.

The depicted anterior vertebral body tethering system 100 also includes installation tool 200. Installation tool 200 broadly includes an actuator handle 210 and a barrel 220. Barrel 220 defines a longitudinal lumen 222. Installation tool 200 includes a hinge 224, a tensioning member 226, and a one-way mechanism 228 which are all coupled to barrel 220. Hinge 224 pivotably couples tensioning member 226 to other fixed portions of barrel 220. In some embodiments, tensioning member 226 is movably coupled to barrel 220 by ways other than by pivotable coupling.

In the depicted embodiment, actuator handle 210 can be manually actuated to pivot tensioning member 226 relative to other fixed portions of barrel 220. In use during a surgery, actuator handle 210 is outside of the patient's body, while barrel 220 extends within the patient's body through an incision in the patient's skin. As described further below, installation tool 200 can be used to sequentially tension segments of tether 130 between adjacent pairs of vertebral screws 110 (e.g., the segment of tether 130 between vertebral screws 110a and 110b in the example provided by FIGS. 3-6).

Referring also to FIG. 4, installation tool 200 is releasably coupleable with vertebral screw 110b in preparation for tensioning the segment of tether 130 between vertebral screws 110a and 110b, and for subsequently engaging end cap 120 with vertebral screw 110b to fixedly secure tether 130 to vertebral screw 110b.

As shown, a distal tip portion of barrel 220 can placed over the head of vertebral screw 110b. That is, a distal end portion of lumen 222 receives the head of vertebral screw 110b so as to mate installation tool 200 with vertebral screw 110b (the head of vertebral screw 110b is shown partially transparent to indicate that it is within lumen 222).

In some cases, features such as dimples 112 on the head of vertebral screw 110b can releasably engage with corresponding structural features (e.g., ball detents) on barrel 220. Such an arrangement can serve to releasably detain installation tool 200 on the head of vertebral screw 110b, and serve to provide tactile feedback to the surgeon indicating that installation tool 200 is properly coupled with vertebral screw 110b. Barrel 220 includes relief areas (e.g., slots) that provide clearance for the passage of tether 130 laterally through the distal tip portion of barrel 220. In some embodiments, while the distal tip portion of barrel 220 is on the head of vertebral screw 110b, one-way mechanism 228 and/or tensioning member 226 is/are engaged with tether 130 (e.g., engaged with an expanded area 132, or engaged with portions of tether 130 between adjacent expanded areas 132).

Figure 5:
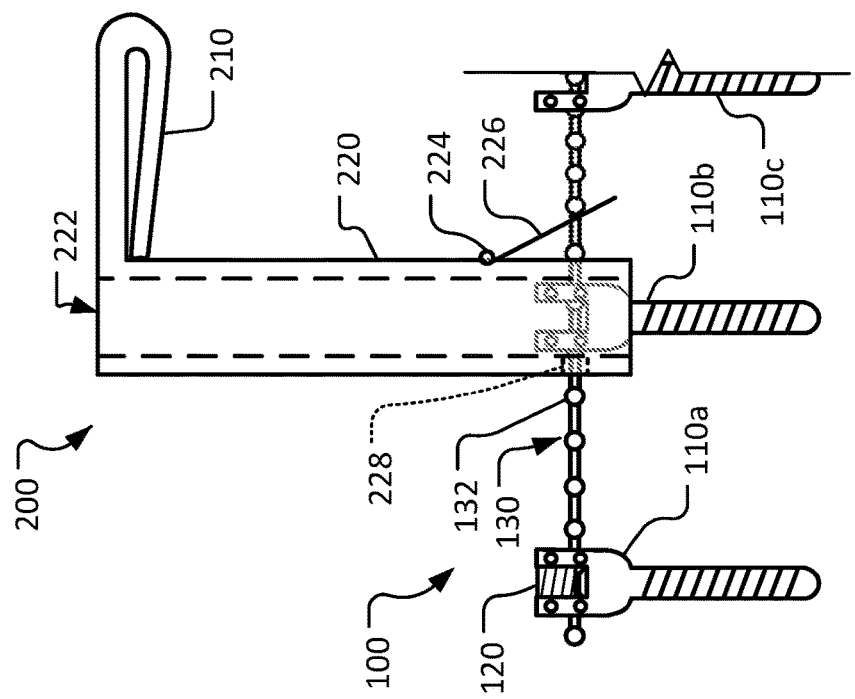
FIG. 5 shows another installation step of the anterior vertebral body tethering system of FIG. 3.

Referring to FIG. 5, while installation tool 200 is engaged with vertebral screw 110b as shown, a clinician-user (e.g., surgeon) can manually actuate actuator handle 210 to cause tensioning member 226 to apply tension to the segment of tether 130 between vertebral screws 110a and 110b. For example, in the depicted embodiment when actuator handle 210 is squeezed, tensioning member 226 pivots in relation to barrel 220 to force tether 130 away from vertebral screw 110a (where tether 130 is fixedly anchored). In result, the segment of tether 130 between vertebral screws 110a and 110b becomes tensioned. In some embodiments, actuator handle 210 includes a ratcheting mechanism that releasably locks and maintains the tension on tether 130 until the tension is released by deactivation of the ratcheting mechanism.

In some embodiments, the tension of tether 130 created by tensioning member 226 is maintained because one-way mechanism 228 allows tether 130 to pass through in one direction, but not in the opposite direction. For example, in FIG. 5 one-way mechanism 228 allows tether 130 to pass to the right (e.g., as tension is applied by tensioning member 226), but not to the left. Accordingly, one-way mechanism 228 can thereby maintain the tension of tether 130 that is applied as a result of actuation of actuator handle 210. In some cases, it is particularly the physical interaction between one-way mechanism 228 and expanded areas 132 (rather than other portions of tether 130) that prevents or inhibits tether 130 from passing leftward in relation to one-way mechanism 228. One-way mechanism 228 can comprise a variety of different designs including, but not limited to, a pawl mechanism, an expandable conical passage, a one-way clutch mechanism, and the like.

Referring to FIG. 6, while the tension of the segment of tether 130 between vertebral screws 110a and 110b is maintained, a clinician can engage an end cap 120 with the head of vertebral screw 110b to fixedly couple/attach tether 130 to vertebral screw 110b, such that the tension of the segment of tether 130 between vertebral screws 110a and 110b is maintained on an on-going basis after the surgery. For example, installation tool 300 can be used to install end cap 120 into threaded engagement with the head of vertebral screw 110b to securely compress tether 130 between end cap 120 and vertebral screw 110b.

In the depicted embodiment, the distal tip portion of installation tool 300 releasably engages with end cap 120

(e.g., using a hex driver and hex socket arrangement). In some cases, an adhesive material such as bone wax can be used between installation tool 300 and end cap 120 to facilitate a secure but temporary engagement there between for the installation process. Installation tool 300 and end cap 120 can be passed through lumen 222 to threadedly place end cap 120 into the head of vertebral screw 110b as shown.

With the end cap 120 secured to vertebral screw 110b such that the tension of the segment of tether 130 between vertebral screws 110a and 110b is maintained on an on-going basis, then the process depicted by FIGS. 3-6 can be repeated for the next vertebral screw (i.e., vertebral screw 110c). After an end cap is secured to vertebral screw 110c such that the tension of the segment of tether 130 between vertebral screws 110b and 110c is maintained on an on-going basis, then the process can be repeated for the next vertebral screw in the sequence, and so on, until all vertebral screws have been so addressed. In such a fashion, tether 130 can be sequentially tensioned to cinched the vertebrae together on one side and splay the vertebrae open on the other side (as shown in FIG. 2) to treat a spine that has scoliosis.

Additional/Alternative Design Features

In some embodiments, one-way mechanism 228 is selectively releasable. That is, in some embodiments while one-way mechanism 228 is maintaining tension on tether 130 a clinician can disengage or deactivate one-way mechanism 228 such that it no longer maintains tension on tether 130.

In some embodiments, one-way mechanism 228 is integrated with the heads of vertebral screws 110.

In some embodiments, installation tool 200 is designed to mechanically couple with the heads of vertebral screws 110 so that installation tool 200 can control/prevent rotation of vertebral screws 110.

In some embodiments, installation tool 200 is designed to measure the tension that is applied to tether 130 via tension meter to quantitate the amount of tension applied.

In some embodiments, installation tool 200 is designed to have a variable length of the barrel to accommodate different chest wall depths.

In some embodiments, installation tool 200 has a large hinge in the middle of the barrel to facilitate the mechanical coupling of screw head to installation tool 200.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain cir-cumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A surgical tool, comprising:
    an actuator handle;
    a barrel extending from the actuator handle, the barrel defining a longitudinal lumen;
    a one-way mechanism coupled to a distal end portion of the barrel, the one-way mechanism configured to engage with a tether such that the one-way mechanism allows passage of the tether in a first direction and prevents passage of the tether in a second direction that is opposite to the first direction; and
    a tensioning member movably coupled to the distal end portion of the barrel, the tensioning member configured to engage with the tether and to apply tension to the tether along the first direction in response to a manual actuation of the actuator handle,
    wherein the one-way mechanism and the tensioning member are disposed on opposite sides of the longitudinal lumen defined by the barrel.

2. The surgical tool of claim 1, wherein the tensioning member is pivotably coupled to the barrel.

3. The surgical tool of claim 1, wherein the actuator handle includes a ratchet mechanism.

4. The surgical tool of claim 1, wherein the one-way mechanism is manually releasable from preventing passage of the tether in the second direction.

5. The surgical tool of claim 1, further comprising a second surgical tool having an elongate shaft that can extend into the longitudinal lumen.

6. The surgical tool of claim 1, wherein the first direction is oriented perpendicular to a longitudinal axis of the barrel.

7. The surgical tool of claim 1, wherein the longitudinal lumen is configured to allow the tether to pass through the longitudinal lumen.

8. The surgical tool of claim 7, wherein the tensioning member is pivotally connected to the barrel.

9. A system for anterior vertebral body tethering, the system comprising:
    a plurality of vertebral screws;
    an elongate tether; and
    a first surgical tool comprising:
        an actuator handle;
        a barrel extending from the actuator handle, a distal tip portion of the barrel being releasably coupleable with each of the vertebral screws individually;
        a one-way mechanism coupled to a distal end portion of the barrel, the one-way mechanism configured to engage with the elongate tether such that the one-way mechanism allows passage of the elongate tether in a first direction and prevents passage of the tether in a second direction that is opposite to the first direction; and a tensioning member movably coupled to the distal end portion of the barrel, the tensioning member configured to engage with the elongate tether and to apply tension to the elongate tether along the first direction in response to a manual actuation of the actuator handle, wherein the one-way mechanism and the tensioning member are disposed on opposite sides of a longitudinal lumen defined by the barrel.

10. The system of claim 9, further comprising a second surgical tool having an elongate shaft that can extend into a lumen defined by the barrel.

11. The system of claim 9, wherein the elongate tether comprises a plurality of expanded areas spaced apart from each other along the elongate tether.

12. The system of claim 11, wherein the tensioning member engages with the expanded areas of the elongate tether.

13. The system of claim 11, wherein the one-way mechanism is configured to engage with the expanded areas of the elongate tether such that the one-way mechanism allows passage of the elongate tether in the first direction and prevents passage of the elongate tether in the second direction.

14. The system of claim 9, wherein the first direction is oriented perpendicular to a longitudinal axis of the barrel.

15. The system of claim 9, wherein the longitudinal lumen is configured to allow the elongate tether to pass through the longitudinal lumen.

16. A method of treating scoliosis of a spine, the method comprising:

anteriorly installing vertebral screws into vertebrae of the spine such that a first vertebra of the vertebrae receives a first vertebral screw of the vertebral screws and a second vertebra of the vertebrae receives a second vertebral screw of the vertebral screws;

fixedly attaching a tether to the first vertebral screw;

releasably coupling a first surgical tool to the second vertebral screw and to the tether concurrently, the first surgical tool comprising:

an actuator handle;

a barrel extending from the actuator handle, a distal tip portion of the barrel being releasably coupleable with each of the vertebral screws individually;

a one-way mechanism coupled to a distal end portion of the barrel, the one-way mechanism configured to engage with the tether such that the one-way mechanism allows passage of the tether in a first direction and prevents passage of the tether in a second direction that is opposite to the first direction; and a tensioning member movably coupled to the distal end portion of the barrel, the tensioning member configured to engage with the tether and to apply tension to the tether along the first direction in response to a manual actuation of the actuator handle, wherein the one-way mechanism and the tensioning member are disposed on opposite sides of a longitudinal lumen defined by the barrel; and manually actuating the actuator handle while the distal tip portion of the barrel is releasably coupled with the second vertebral screw and the tether such that tension is applied to the tether between the first vertebral screw and the tensioning member.

17. The method of claim 16, further comprising, while maintaining the tension applied to the tether between the first vertebral screw and the tensioning member, fixedly attaching the tether to the second vertebral screw such that the tension is thereafter maintained in a portion of the tether between the first vertebral screw and the second vertebral screw without needing the tensioning member to apply the tension in the portion of the tether between the first vertebral screw and the second vertebral screw.

18. The method of claim 16, wherein the first direction is oriented perpendicular to a longitudinal axis of the barrel.

19. The method of claim 16, wherein the longitudinal lumen is configured to allow the tether to pass through the longitudinal lumen.

* * * * *